United States Patent [19]
Duer

[11] Patent Number: 5,507,761
[45] Date of Patent: Apr. 16, 1996

[54] EMBOLIC CUTTING CATHETER

[76] Inventor: Edward Y. Duer, No. 31-2 Megamiyama-cho, Koyoen, Nishinomiya 662, Japan

[21] Appl. No.: 320,246

[22] Filed: Oct. 11, 1994

[51] Int. Cl.$^6$ ............................................. A61B 17/22
[52] U.S. Cl. ................................. 606/159; 606/180
[58] Field of Search ........................ 606/159, 172, 606/171, 180, 170

[56] References Cited

U.S. PATENT DOCUMENTS

| | | | |
|---|---|---|---|
| 4,994,067 | 2/1991 | Summers | 606/159 |
| 5,135,483 | 8/1992 | Wagner et al. | 604/22 |
| 5,287,858 | 2/1994 | Hammerslag et al. | 128/772 |
| 5,364,395 | 11/1994 | West, Jr. | 606/46 |

Primary Examiner—Michael H. Thaler
Assistant Examiner—Patrick W. Rasche
Attorney, Agent, or Firm—Roy A. Ekstrand

[57] ABSTRACT

An embolic cutting catheter includes an elongated generally cylindrical catheter body having a forward end and an interior passage extending therethrough. An elongated flexible guide wire is received within the interior passage and extends to the forward end. A circular baseplate receives and supports a dome-shaped cutter head and overlying safety guard. The safety guard, cutter head, and baseplate are rotatable as a common unit in response to rotation of the guide wire. In an alternate embodiment, the safety guard is formed of a flexible material and resiliently supported by a resilient guard support situated within a channel formed in the cutter head. In a further alternate embodiment, the safety guard defines a cruciform shape.

12 Claims, 1 Drawing Sheet

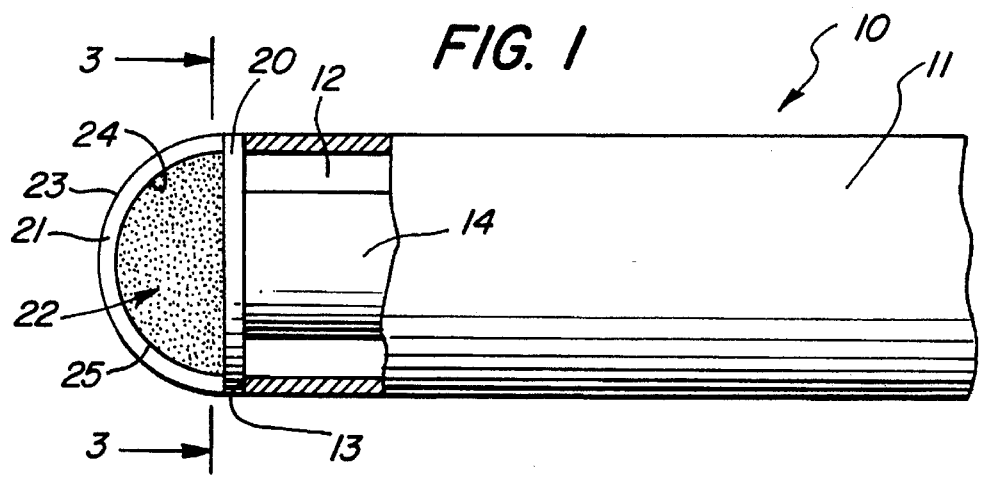
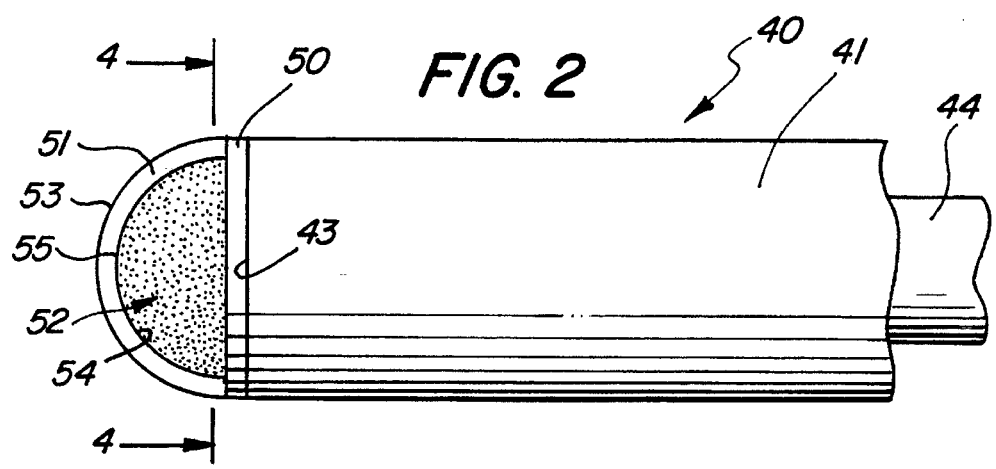
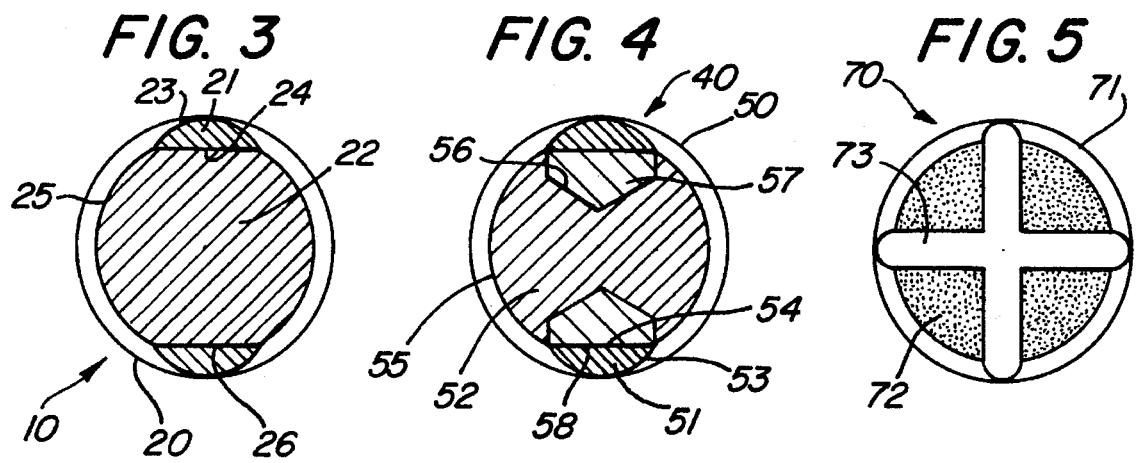

EMBOLIC CUTTING CATHETER

FIELD OF THE INVENTION

This invention relates generally to removal of atheromatous plaque from blood vessels and particularly to cutting catheter apparatus used therefor.

BACKGROUND OF THE INVENTION

A serious problem to humans and higher order primates is the accumulation of atheromatous plaque material which attaches itself to the inner walls of blood vessels and begins a build-up of plaque which gradually decreases the available flow passages within, for example, a coronary or other artery. If left untreated, such atheromatous plaque will lead to partial or total blockage of blood flow to the affected portions of the body normally supplied by such blocked or partially blocked arteries. This in turn may lead to serious injury, impairment, or even death.

In cases of serious blood vessel blockages due to build-up of embolic plaque material, the use of one or more methods of removal must be implemented to avoid the need for more life-threatening surgical procedures involving opening the chest for bypass surgery, or the like.

To meet this need, a variety of plaque removal devices have been designed which typically utilize a cutting head supported by an elongated catheter member coupled to a drive mechanism for operating a cutting head. The cutting head is typically composed of a rigid material such as stainless steel or the like which has been impregnated with an abrasive such as diamond powder. The cutting head is manipulated such that the cutting head works to displace the plaque build-up from the inner arterial walls and to crush it into a fine particle structure which may be removed from the circulatory system by the liver.

The effectiveness and desirability of such conventional plaque removal devices is generally limited by two significant problems. First, the use of a sharp high-speed cutting tool inserted within the delicate inner arterial passages exposes the patient to substantial risk of damage to the arterial walls as the cutter operates. In response to this problem, practitioners attempt to provide devices which are safer in operation. However, structures designed to avoid or minimize risk of damage to the arterial walls presented by such cutters usually employ some alignment apparatus which raises the second problem. Such alignment apparatus itself may block or obscure the artery during the procedure and subjecting the patient to further risk and potential injury.

Thus, there remains a continuing need in the art for evermore improved, safer to operate and less injurious emboli cutting catheters which are nonetheless effective in their cutting action.

SUMMARY OF THE INVENTION

Accordingly, it is a general object of the present invention to provide an improved emboli cutting catheter. It is a more particular object of the present invention to provide an improved embolic cutting catheter which provides effective plaque removal without subjecting the patient to serious risk of arterial damage and without subject the patient to obstruction of blood flow during the procedure.

In accordance with the invention, there is provided for use in the present invention for the clearing of the obstructed blood vessel while protecting the blood vessel from injury, a novel cutting catheter of the present invention which comprises: an elongated, generally cylindrical catheter body defining a forward end and an interior passage; an elongated flexible drive guide wire extending through the interior passage of the catheter body and securing to the forward catheter head; a dome-shaped cutter head received within the aperture of the disk-shaped cutter head base support component and defining a convex abrasive portion.

The cutter head component comprises a dome shaped cutter head and one or more safety guards having generally elevated smooth mound-like surfaces each of which may be rigid and fixed in position or may be flexible and movable. In the latter case, a soft, sponge-like material is contained within the inside catheter head diameter for resiliently supporting the safety guards.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 1 sets forth a partial section view of an embolic cutting catheter constructed in accordance with the present invention;

FIG. 2 sets forth a partial side view of an alternate embodiment of the present invention embolic cutting catheter;

FIG. 3 sets forth a section view of the embodiment of FIG. 1 taken along section lines 3—3 therein;

FIG. 4 sets forth a section view of the embodiment of the present invention of FIG. 2 taken along section lines 4—4 therein; and FIG. 5 sets forth a front view of a still alternate embodiment of the present invention embolic cutting catheter.

DESCRIPTION OF THE PREFERRED EMBODIMENTS

FIG. 1 sets forth a partial section view of a cutting catheter head constructed in accordance with the present invention and generally referenced by numeral 10. Catheter head 10 includes an elongated generally cylindrical body 11 defining a forward end 13 and an interior passage 12. The remaining end of catheter body 11 (not shown) is in accordance with conventional fabrication techniques coupled to conventional apparatus for catheter insertion (not shown). Catheter head 10 further includes an elongated flexible guide wire 14 extending through interior passage 12. A circular base plate is secured to the interior end of guide wire 14 using conventional fabrication techniques and defines an outer diameter generally corresponding to the diameter of catheter body 11. The remaining end of guide wire 14 (not shown) extends outwardly through interior passage 12 and is coupled to a conventional means for rotation (not shown) which imparts rotation to guide wire 14. Catheter head 10 further includes a generally hemispherical domed-shaped cutter head 22 defining an abrasive outer surface 25. Catheter head 22 is secured to base plate 20 and rotatable therewith as guide wire 14 is rotated. In accordance with an important aspect of the present invention, a curved safety guard 21 is secured to baseplate 12 and defines a concave interior surface 24 generally conforming to and overlying a diametric portion of abrasive surface 25. Safety guard 21 further defines a convex outer surface 23. Safety guard 21 is secured to baseplate 20 and rotatable therewith.

In operation, conventional rotation means (not shown) rotate guide wire 14 within interior passage 12 producing a corresponding rotation of the combined structure of baseplate 20, cutter head 22 and safety guard 21 within the interior of the target arterial walls. In accordance with an important aspect of the present invention, the soft pliable inner arterial walls of the host blood vessel are touched solely by safety guard 12 which deforms the arterial walls and separates them from abrasive surface 25 of cutter head 22. This in turn permits the insertion of catheter body 11 through the inner arterial walls without risk of blood vessel damage. Embolic plaque attached to the inner surface of the arterial walls is moved by safety guard 21 away from abrasive surface 25. As catheter head 10 is inserted and cutter head 22, baseplate 20 and safety guard 21 are rotated, the interior arterial walls are contacted solely by safety guard 21 while abrasive surface 25 of cutter head 22 cuts and emulsifies the plaque for return to the circulatory system and absorption by phagocytes and removal from the patient's body after passing through the liver. Alternatively, such emulsified debris may be removed using conventional suction catheter methods operative upon catheter body 11 through interior passage 12.

Thus, in accordance with an important aspect of the present invention, the rotating structure provided by the combination of baseplate 20, cutter head 22 and safety guard 21 rotating a single unit provides effective embolic cutting and emulsifying action while protecting delicate arterial walls. It will be apparent to those skilled in the art that while a single safety guard 21 is shown in FIG. 1, one or more additional safety guards or safety guard segments similarly structured may be secured to baseplate 20 and extend across underlying portions of abrasive surface 25 without departing from the spirit and scope of the present invention. For example and with temporary reference to FIG. 5, a pair of safety guards such as safety guard 21 having a center intersection are shown forming a combined safety guard 73 having a generally cruciform shape. In addition, it will apparent to those skilled in the art that other numbers of safety guard or safety guard segments such as safety guard 21 may be used in other combinations such as the use of three segments of safety guard 21 commonly joined at a center intersection to form a "Y-shaped" safety guard. The essential aspect of the present invention is the provision of safety guard 21 extending beyond abrasive surface 25 of cutter head 22 and rotatable therewith to protect delicate arterial walls.

FIG. 2 sets forth an alternate embodiment of the present invention embolic cutting catheter having a catheter head generally referenced by numeral 40. Catheter head 40 includes a catheter body 41 having a generally cylindrical shape and defining an interior passage identical to interior passage 12 of catheter body 11 shown in FIG. 1. Catheter body 41 further includes a forward end 43 and receives an elongated flexible guide wire 44. Catheter body 41 and guide wire 44 extend from catheter head 40 to appropriate catheter insertion means and guide wire rotation means (not shown). Catheter head 40 further includes a circular baseplate 50 having an outer diameter generally corresponding to the diameter of catheter body 41. While not seen in FIG. 2, it should be understood that the interior end of guide wire 44 is secured to baseplate 50 in accordance with conventional attachment apparatus and in a similar manner to that shown for baseplate 20 and guide wire 14 in FIG. 1. The essential feature of this attachment is that baseplate 50 is rotatable in combination with guide wire 44.

In further accordance with the present invention, catheter head 40 includes a semispherical dome-shaped cutter head 52 having an abrasive surface 55 formed thereon. Abrasive surface 55 may, for example, be formed using a conventional diamond dust abrasive grit or other suitable material. A safety guard 51 is secured to baseplate 50 and defines a concave interior surface 54 corresponding generally to abrasive surface 55 and overlying a portion thereof together with an outer surface 53. In accordance with the present invention, baseplate 50, cutter head 52, and safety guard 51 rotate as a common unit in response to rotation of guide wire 44 with respect to catheter body 40.

The embodiment of FIG. 2 differs from the embodiment shown in FIG. 1 in that safety guard 51 is formed of a flexible material and is resiliently supported upon cutter head 52 in the manner shown in FIG. 4. Thus, the embodiment of FIG. 2 provides a further safety aspect for the present invention catheter head in that safety guard 51 is flexible and therefore movable in response to forces applied to safety guard 51. The flexibility of safety guard 51 also improves the embolic cutting performance of catheter head 40.

In operation, catheter head 40 is inserted into the host blood vessel and guide wire 44 is rotated producing rotation of the combined structure of baseplate 50, safety guard 51 and cutter head 52. During this rotation, the arterial walls are contacted by safety guard 51 and maintained out of contact with abrasive surface 55. Thus, the blood vessel walls are protected from the abrasive surface. When embolic plaque is contacted, however, the flexibility of safety guard 51 and its resilient support upon cutter head 52 permit safety guard 51 to flex inwardly allowing the embolic plaque to be directly contacted by abrasive surface 55. This improves the cutting and emulsifying action of abrasive surface 55 and improves the overall performance of catheter head 40.

Thus, the performance of catheter head 40 provides reliable safe protection of the delicate interior walls of blood vessels while providing effective cutting and emulsifying of embolic plaque.

FIG. 3 sets forth a section view of catheter head 10 taken along section lines 3—3 in FIG. 1. As described above, baseplate 20 defines a circular outer diameter corresponding generally to catheter body 11. As is also described above, catheter head 22 is generally semispherical defining an abrasive surface 25. Cutter head 22 further defines a generally cylindrical surface 26. Accordingly, safety guard 21 defines a corresponding cylindrical interior surface 24 which conforms generally to surface 26. Safety guard 21 is secured to surface 26 using a convenient attachment such as adhesive attachment or the like. Safety guard 21 further defines a convexly curved outer surface 23 extending from interior surface 24. Curved outer surface 23 and interior surface 24 combine to provide a generally D-shaped cross-section for safety guard 21. In its preferred form, safety guard 21 is fabricated of substantially rigid material and is securely attached to baseplate 20 and cutter head 22. Thus, baseplate 20, safety guard 21 and cutter head 22 having abrasive surface 25 is rotated as a single integral unit in response to the above-described rotation of guide wire 14 (shown in FIG. 1).

FIG. 4 sets forth a section view of catheter head 40 taken along section lines 4—4 in FIG. 2. As described above, catheter head 40 includes a circular baseplate 50 and a generally dome-shaped semispherical cutter head 52 having an abrasive outer surface 55. Cutter head further defines an inwardly extending channel 56 which receives a resilient guard support 57 in a secure attachment. Resilient guard 57 fills channel 56 and is secured therein using conventional attachment means such as adhesive attachment or the like. Resilient guard 57 further defines a cylindrical outer surface 58. Safety guard 51 defines a concave interior surface 54 corresponding generally to surface 58 and a curved outer surface 53. Curved outer surface 53 and interior surface 54 combine to provide a generally D-shaped cross-section for safety guard 51.

In accordance with an important advantage of catheter head 40, safety guard 51 is fabricated of a flexible material and is resiliently supported by guard support 57. As a result, safety guard 51 is secured to baseplate 50 and cutter head 52 in a resilient manner which permits safety guard 51 to flex or deform temporarily when encountering embolic plaque during the embolic cutting operation. In its preferred form, however, the resilience of guard support 57 and the flexibility of safety guard 51 are selected to assure that safety guard 51 generally maintains its normal shape while contacted by soft interior walls of the patient's arteries. Thus, safety guard 51 maintains its general shape in response to soft arterial wall tissue while flexing in response to embolic plaque to simultaneously provide effective protection of arterial walls and effective cutting of embolic plaque.

FIG. 5 sets forth a front view of a still further alternate embodiment of the present invention cutting catheter having a cutting head generally referenced by numeral 70. Catheter head 70 includes a circular baseplate 71 supporting a generally dome-shaped cutter head 72 together with a cruciform-shaped safety guard 73. Safety guard 73 and cutter head 72 are secured to baseplate 71 such that the combination of baseplate 71, cutter head 72 and safety guard 73 rotate as a single unit in the above-described embolic cutting operation. In all other respects, the embodiment of FIG. 5 is substantially identical in operation and benefit to the embodiments shown in FIGS. 1 and 2.

What has been shown is an embolic cutting catheter providing an effective dome-shaped cutter head having an abrasive surface together with a outer safety guard rotatable with the cutting head to protect delicate interior walls of the patient's arteries during the embolic cutting process. The present invention utilizes either a rigid safety guard or, alternatively, a resiliently supported flexible safety guard. The latter is capable of flexing in response to embolic plaque within the blood vessel to improve the cutting and pulverizing action of the cutter head without risking injury to the inner walls of the patient's arteries.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. For use in clearing an obstructed blood vessel, a cutting catheter comprising:
   an elongated generally cylindrical catheter body defining a forward end and an interior passage;
   an elongated flexible drive guide wire extending through said interior passage and having an interior end;
   a base support coupled to said interior end of said drive guide wire;
   a generally dome-shaped cutter head coupled to said base and defining a convex abrasive outer surface; and
   a safety guard fixably attached to said base support and extending across a portion of said abrasive outer surface,
   said drive guide wire, said base support, said cutter head and said safety guard rotating with respect to said catheter body as said drive guide wire is rotated.

2. A cutting catheter as set forth in claim 1 wherein said safety guard defines an interior concave surface conforming generally to said convex abrasive outer surface of said cutter head.

3. A cutting catheter as set forth in claim 2 wherein said safety guard defines an outer convex surface conforming generally to said convex abrasive surface.

4. A cutting catheter as set forth in claim 3 wherein said cutter head defines a generally cylindrical surface portion and wherein said concave interior surface of said safety guard is correspondingly cylindrical and conforms thereto.

5. A cutting catheter as set forth in claim 4 wherein said convex outer surface of said safety guard is curved outwardly from said concave interior surface such that said safety guard defines a generally D-shaped cross-section.

6. A cutting catheter as set forth in claim 5 wherein said safety guard is formed of a rigid material.

7. A cutting catheter as set forth in claim 3 wherein said cutter head defines a recessed channel extending inwardly from said abrasive surface and a resilient element supported within said channel and wherein said safety guard overlies said resilient element.

8. A cutting catheter as set forth in claim 7 wherein said safety guard is formed of a flexible material.

9. A cutting catheter as set forth in claim 8 wherein said resilient element defines a generally cylindrical outer surface and wherein said concave interior of said safety guard is correspondingly cylindrical and conforms thereto.

10. A cutting catheter as set forth in claim 9 wherein said convex outer surface of said safety guard defines a greater radius of curvature than said dome-shaped abrasive surface of said cutter head.

11. A cutting catheter as set forth in claim 10 wherein said convex outer surface of said safety guard is curved outwardly from said concave interior surface such that said safety guard defines a generally D-shaped cross-section.

12. A cutting catheter as set forth in claim 3 wherein said safety guard is generally cruciform-shaped.

\* \* \* \* \*